United States Patent [19]

Samain et al.

[11] Patent Number: 5,520,706
[45] Date of Patent: May 28, 1996

[54] PROCESS FOR THE OXIDATION DYEING OF KERATINOUS FIBERS USING WATER VAPOR

[75] Inventors: Henri Samain, Bievres; Jean-Michel Sturla, Saint-Cloud, both of France

[73] Assignee: L'Oreal, Paris, France

[21] Appl. No.: 357,754

[22] Filed: Dec. 16, 1994

[30] Foreign Application Priority Data

Dec. 22, 1993 [FR] France ................... 93 15481

[51] Int. Cl.⁶ ..................... A61K 7/13
[52] U.S. Cl. ............... 8/406; 8/405; 8/408; 8/933; 132/208
[58] Field of Search ............ 8/405, 408, 406, 8/933; 132/208

[56] References Cited

U.S. PATENT DOCUMENTS

| | | | |
|---|---|---|---|
| 4,166,473 | 9/1979 | Bauer et al. | 132/9 |
| 4,217,914 | 8/1990 | Jacquet et al. | 132/7 |
| 4,341,229 | 7/1982 | Bauer et al. | 132/7 |
| 4,422,853 | 12/1983 | Jacquet et al. | 8/406 |
| 4,553,339 | 11/1985 | Rigo | 34/99 |
| 4,904,275 | 2/1990 | Grollier | 8/408 |
| 4,948,579 | 8/1990 | Jacquet et al. | 424/72 |
| 5,196,189 | 3/1993 | Jacquet et al. | 424/72 |

FOREIGN PATENT DOCUMENTS

| | | |
|---|---|---|
| 496653 | 7/1992 | European Pat. Off. |
| 1011151 | 6/1952 | France . |
| 2270846 | 12/1975 | France . |
| 2273492 | 1/1976 | France . |
| 2575067 | 6/1986 | France . |
| 4235436 | 4/1993 | Germany . |
| 357161 | 4/1958 | Switzerland . |

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A process for the oxidation dyeing of keratinous fibers, characterized in that it comprises contacting the fibers, in the presence of an oxidizing agent, with a composition containing at least one oxidation dye and with a gas containing water vapor, the temperature of the gas being at least 75° C., preferably greater than 75° C., and the contact time not exceeding two minutes, preferably less than two minutes. The hair is dyed uniformly over the whole head of hair, from the roots to the ends, regardless of the condition of the hair.

14 Claims, No Drawings

PROCESS FOR THE OXIDATION DYEING OF KERATINOUS FIBERS USING WATER VAPOR

The present invention is directed to a process for the oxidation dyeing (or colouring) of keratinous fibers using water vapour and to a composition comprising at least one oxidation dye.

It is known to dye keratinous fibres, and in particular human keratinous fibres such as hair, with dye compositions containing oxidation dye precursors. Typical dye precursors, also known as "oxidation bases," include ortho- or para-phenylenediamines and ortho- or para-aminophenols. These precursors are usually combined with couplers, also known as coloration modifiers, which include meta-phenylenediamines, meta-aminophenols and meta-diphenols. The couplers enable the "background" colours obtained with the products of condensation of the oxidation bases to be modified and to be enriched with glints.

However, this type of dyeing process, which also requires the use of an oxidizing agent such as hydrogen peroxide, gives poor dyeing results when the keratinous fibres to be dyed are very sensitized (i.e., "damaged"). Thus, this type of oxidation dyeing has the drawback of being selective with regard to the fibres to be dyed.

The selectivity of a dye is referred to as the difference in uptake, i.e., in dyeing power, of the dye on the hair fibres. The selectivity depends on whether the hair has been sensitized to a greater or lesser extent, either by a treatment such as a bleaching or a permanent wave, or by atmospheric agents, especially in the case of the ends of the hair. The dyeing results obtained on hair having differences in sensitization are thus heterogeneous. These irregularities are obviously undesirable from an aesthetic point of view. The present invention aims to resolve this problem.

It has now been discovered, surprisingly, that the use of a gas comprising water vapour, heated to a temperature of at least 75° C., preferably greater than 75° C., on hair treated with a composition comprising at least one oxidation dye, and in the presence of an oxidizing agent, produces dyeing results that show little or no dependence at all on the degree of sensitization of the keratinous fibres prior to dyeing. The present invention permits the hair to be dyed uniformly over the whole head of hair, from the roots to the ends, regardless of the condition of the hair.

The use of water vapour in an oxidation dyeing process has been described in French Patent No. 1,011,151, the disclosure of which is incorporated by reference. This French patent teaches the use of water vapour heated to approximately 50° C. to accelerate the process of dyeing the hair, while at the same time reducing the amounts of dyes used. At 50° C., however, there is no decrease in the selectivity problem discussed previously.

The present invention is thus directed to a process for the oxidation dyeing of keratinous fibres comprising the step of contacting the fibres, the fibres having been previously contacted with a composition containing at least one oxidation dye, in the presence of an oxidizing agent, with a gas containing water vapour, the temperature of the gas being at least 75°, preferably greater than 75° C., for a contact time between the gas and the fibres to be dyed not exceeding two minutes, preferably less than two minutes.

The present invention also contemplates a process for the oxidation dyeing of keratinous fibres comprising the step of contacting the fibres, in the presence of an oxidizing agent, with a composition containing at least one oxidation dye and with a gas containing water vapour, the temperature of the gas and the contact time between the gas and the fibres being sufficient to substantially uniformly dye the fibres.

A further embodiment of the present invention includes a process for the oxidation dyeing of keratinous fibres, comprising the step of contacting the fibres, in the presence of an oxidizing agent, with a composition containing at least one oxidation dye and with a gas containing water vapour, the temperature of the gas being at least 75° C., preferably being greater than 75° C., and the contact time between the gas and the fibres being sufficient to substantially uniformly dye the fibres.

A still further embodiment contemplated by the present invention is a process for the oxidation dyeing of keratinous fibres, comprising the step of contacting the fibres, in the presence of an oxidizing agent, with a composition containing at least one oxidation dye and with a gas containing water vapour, for a time not exceeding two minutes, preferably less than two minutes, and wherein the gas has a temperature sufficient to substantially uniformly dye the fibres.

The present invention is also directed to a process for the oxidation dyeing of keratinous fibres, comprising the step of contacting the fibres, in the presence of an oxidizing agent, with a composition containing at least one oxidation dye and with a gas containing water vapour, the temperature of the gas being at least 75° C., for a contact time between the gas and the fibres to be dyed not exceeding two minutes.

The process of the present invention is used for the oxidation dyeing of keratinous fibres in general. The preferred form of keratinous fibres taught by this invention is human keratinous fibres, such as hair.

The water vapour can be transported by a carrier gas that may additionally contain solvent vapour. As the vapour, gases such as oxygen and nitrogen, gas mixtures such as air or vaporizable compounds can be used. The solvents used in these vapours are cosmetically acceptable organic solvents such as alcohols, glycols or glycol ethers. Suitable alcohols may include ethanol, isopropanol, benzyl alcohol and phenethyl alcohol. Typical glycols and glycol ethers include the monomethyl, monoethyl and monobutyl ethers of ethylene glycol, propylene glycol, butylene glycol and dipropylene glycol, as well as alkyl ethers such as diethylene glycol monobutyl ether.

The gas preferably comprises at least 1% by volume of water vapour relative to the total volume of the gas. The gas preferably contains either exclusively or essentially water vapour or a mixture of water vapour and air. The temperature of the gas is at least 75° C., and preferably greater than 75° C. More preferably, the temperature of the gas is at least 85° C. and still more preferably the temperature of the gas ranges from 85° to 150° C. Even more preferably, the temperature of the gas ranges from 75° C. to less than 100° C., and most preferably ranges from 90° C. to less than 100° C.

During the process of the present invention, the gas contacts the fibres to be dyed for a period preferably ranging from 0.01 second to less than two minutes, more preferably, for a period ranging from 0.1 second to 50 seconds, and most preferably, for a period ranging from 1 to 10 seconds. Application of the gas may be repeated several times on the same fibres, with each application preferably being conducted for a time period as prescribed above.

In a preferred embodiment of the present inventive process, a dye composition containing at least one oxidation dye is applied to the hair, and the hair is subsequently subjected to the action of the water vapour. Another embodiment of the present invention contemplates applying the dye composition and the gas comprising water vapour simultaneously. It is also possible for all or part of the dye composition to be put on the hair by means of the gas flow when some or all of the constituents of the dye composition can be entrained or vaporized.

Regarding the oxidizing agent, it can either be added to the dye composition before use or applied simultaneously with or just after the dye composition in a suitable support. The suitable support may be an aqueous composition or the gas containing the water vapour itself. In a preferred embodiment of the invention, the application of water vapour is followed by rinsing with water.

The production of a hot gas containing the water vapour may be achieved using any apparatus known per se. An apparatus such as that described in French Patent FR-B-2,273,492, or its U.S. counterpart, U.S. Pat. No. 4,166,473, the disclosures of which, including the drawings, are incorporated by reference, may be used as well as any other equivalent apparatus.

The oxidation dyes are selected from oxidation bases and mixtures of oxidation bases and couplers. The oxidation dyes, bases and couplers are products that are well-known in the state of the art. Dyes of this type are disclosed, for example, in French Patent No. FR-B-2,575,067, in U.S. Pat. No. 4,904,275, and in European Patent Application No. EP-A-496,653, the disclosures of which are incorporated by reference. An oxidation dye used in the process of the present invention may be present in concentrations preferably ranging from approximately 0.001% to 10% by weight, relative to the total weight of the dye composition. One or more oxidation dyes may be used.

The oxidizing agent is preferably chosen from hydrogen peroxide, urea peroxide, alkali metal bromates, and persalts such as perborates and persulphates. Hydrogen peroxide is particularly preferred. The concentration of the hydrogen peroxide preferably ranges from 1 to 20 volumes, i.e., from 0.3% by weight to 6% by weight relative to the total weight of the dye composition.

The pH of the dye composition generally ranges from approximately 3 to 11. The pH may be adjusted to the desired value using either basifying or acidifying agents commonly used in the dyeing of keratinous fibres. The basifying agents can include aqueous ammonia, alkali metal carbonates, alkanolamines such as mono- di- and triethanolamines and their derivatives, sodium hydroxide or potassium hydroxide. Inorganic or organic acids like hydrochloric acid, tartaric acid, citric acid and phosphoric acid represent typical acidifying agents.

The pH of the composition containing the oxidizing agent is chosen such that, after mixing with the dye composition, the pH of the resulting composition to be applied to the keratinous fibres preferably ranges from 3 to 11. The pH of the resulting composition may be adjusted to the desired value using acidifying agents or, optionally, basifying agents, which are well-known in the state of the art, in particular agents such as those described above.

The oxidizing composition preferably contains hydrogen peroxide. The dye compositions may also contain, in a preferred embodiment, anionic, cationic, nonionic or amphoteric surface-active agents or mixtures thereof. These surface-active agents are well-known in the state of the art. They are preferably present in proportions ranging from approximately 0.5% to 55% by weight, and more preferably ranging from 2% to 50% by weight, relative to the total weight of the dye composition.

The dye compositions may also contain organic solvents for dissolving components that would not be sufficiently soluble in water. Preferred organic solvents include $C_1$–$C_4$ lower alkanols such as ethanol, isopropanol and glycerol; glycols or glycol ethers such as 2-butoxyethanol, propylene glycol and diethylene glycol monoethyl ether and monomethyl ether; aromatic alcohols such as benzyl alcohol or phenoxy ethanol; analogous products; and mixtures thereof. These solvents are preferably present in proportions ranging from approximately 1% to 40% by weight, and more preferably from 5% to 30% by weight, relative to the total weight of the dye composition.

The dye compositions may additionally contain organic or inorganic thickening agents. Suitable organic thickening agents include acrylic acid polymers, which can be crosslinked, while bentonire represents an acceptable or inorganic thickening agent. The thickening agents are preferably present in proportions ranging from approximately 0.1% to 5%, and more preferably, ranging from 0.2% to 3% by weight relative to the total weight of the dye composition.

Antioxidants may also be introduced into the dye compositions. They are preferably chosen from sodium sulphite, thioglycolic acid, thiolactic acid, sodium bisulphite, dehydroascorbic acid, hydroquinone, 2-methylhydroquinone, 2-tert-butylhydroquinone, and homogentisic acid. They are generally present in proportions ranging from approximately 0.05% to 1.5% by weight relative to the total weight of the dye composition.

The dye compositions may also contain other cosmetically acceptable adjuvants. These adjuvants may include penetration agents, sequestering agents, fragrances, buffers, dispersing agents, treating agents, conditioning agents, film-forming agents, preserving agents and opacifying agents.

The dye composition used in the process according to the present invention may be used in forms convenient for dyeing hair. Examples of convenient forms for the dye composition include liquids, which have been thickened or gelled to some extent, cream, aerosol foam or any other form suitable for dyeing hair.

The examples which follow illustrate the invention, but should not be construed as limiting in nature.

EXAMPLES

EXAMPLE 1 (Invention)

The following dye composition was prepared:

| | |
|---|---|
| Resorcinol | 0.01 g |
| Para-phenylenediamine | 0.4 g |
| Para-aminophenol | 0.24 g |
| 1-Methyl-2-hydroxy-4-(2'-hydroxyethyl)-aminobenzene | 1.2 g |
| Polyoxyethylenated nonylphenol containing 9 mol of ethylene oxide | 3 g |
| Oleyl alcohol | 18 g |
| Polymer consisting of repeating units of formula: | 3 g |

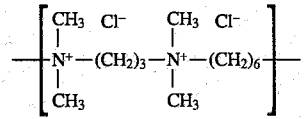

prepared according to French Patent No. 2,270,846, U.S. Pat. No. 4,217,914, U.S. Pat. No. 4,422,853, U.S. Pat. No. 4,948,579, and U.S. Pat. No. 5,196,189, the disclosures of which are incorporated by reference;

| | |
|---|---|
| Ethyl alcohol | 9 g |
| Benzyl alcohol | 11 g |
| Ethylenediaminetetraacetic acid | 0.2 g |
| Aqueous ammonia (containing 22% of $NH_3$) | 12.9 g |
| Monoethanolamine | 6.5 g |
| Ammonium thiolactate (50% thiolactic acid AM (active material)) | 0.8 g |
| 1-Phenyl-3-methyl-5-pyrazolone | 0.15 g |

| | |
|---|---|
| Demineralized water qs (quantity sufficient) | 100 g |

This composition was mixed weight for weight with 20 volumes, i.e., 6% by weight, of hydrogen peroxide at the time of use. The resultant mixture was applied to a lock of bleached hair (alkaline solubility AS20), (lock No. 1) and to a lock of the same hair which had undergone two permanent was (lock No. 2). Alkaline solubility AS20 is a method known to those skilled in the art to determine the degree of hair sensitization. Two jets of water vapour at 90° C. were then applied to the two locks of hair for 30 seconds each. The locks were washed with a standard shampoo and then dried.

The chromatic coordinates in the system L, a, b were measured on both locks with a MINOLTA CHROMAMETER CR200 colorimeter. This measurement permitted a determination of the difference in luminance (ΔL) between lock No. 2 ($L_2$) and lock No. 1 ($L_1$) which was determined as follows:

$\Delta L = L_2 - L_1 = -1.7$

It was thus observed that the shades were more or less identical.

EXAMPLE 2 (comparative)

The mixture of Example 1 was applied to a lock of bleached hair (alkaline solubility AS20), (lock No. 1) and to a lock of the same hair which had undergone two permanent waves (lock No. 2). The composition was left in place for 30 minutes at room temperature. The locks were washed with a standard shampoo and then dried.

The chromatic coordinates in the system L, a, b were measured on both locks with a MINOLTA CHROMAMETER CR200 colorimeter. The difference in luminance (ΔL) between lock No. 2 and lock No. 1 was as follows:

$\Delta L = L_2 - L_1 = 9.8$

Lock No. 2 was much paler in colour than lock No. 1. The difference in colour between these two locks, which were dyed by a comparative process, was very noticeable.

EXAMPLE 3 (comparative)

The mixture of Example 1 was applied to a lock of bleached hair (alkaline solubility AS20), (lock No. 1) and to a lock of the same hair which had undergone two permanent waves (lock No. 2). A jet of water vapour at 50° C. was then applied to the two locks of hair for one minute. The locks were washed with a standard shampoo and then dried.

The chromatic coordinates in the system L, a, b were measured on both locks with a MINOLTA CHROMA METER CR200 colorimeter. The difference in luminance (ΔL) between lock No. 2 ($L_2$) and lock No. 1 ($L_1$) was as follows:

$\Delta L = L_2 - L_1 = 9$

Lock No. 2 was much paler in colour than lock No. 1. The difference in colour between these two locks, comparative which were dyed by a process, was very noticeable.

EXAMPLE 4 (comparative)

The process was performed in the same way as in Example 3, except that the water vapour was applied at 50° C. for 15 minutes.

The chromatic coordinates in tile system L, a, b were measured on both locks with a MINOLTA CHROMAMETER CR200 colorimeter. The difference in luminance (ΔL) between lock No. 2 ($L_2$) and lock No. 1 ($L_1$) was as follows:

$\Delta L = L_2 - L_1 = 5$

Lock No. 2 was much paler in colour than lock No. 1. The difference in colour between these two locks, which were dyed by a comparative process, was very noticeable.

EXAMPLE 5 (Invention)

The following dye composition was prepared:

| | |
|---|---|
| Para-phenylenediamine | 0.65 g |
| Para-aminophenol | 0.03 g |
| Resorcinol | 0.25 g |
| 1-Methyl-2-hydroxy-4-(2'-hydroxyethyl)-aminobenzene | 0.02 g |
| Polyoxyethylenated nonylphenol containing 9 mol of ethylene oxide | 3 g |
| Oleyl alcohol | 18 g |
| Polymer consisting of repeating units of formula: 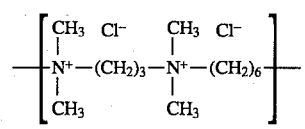 prepared according to French Patent No. 2,270,846, or according to U.S. Pat. Nos. 4,217,914, 4,422,853, 4,948,579, and 5,196,189 | 3 g |
| Ethyl alcohol | 9 g |
| Benzyl alcohol | 11 g |
| Ethylenediaminetetraacetic acid | 0.2 g |
| Aqueous ammonia (containing 22% of $NH_3$) | 12.9 g |
| Monoethanolamine | 6.5 g |
| Ammonium thiolactate (50% thiolactic acid AM) | 0.8 g |
| 1-Phenyl-3-methyl-5-pyrazone | 0.15 g |
| Demineralized water qs | 100 g |

This composition was mixed weight for weight with 20 volume hydrogen peroxide at the time of use. The mixture obtained above was applied to naturally grey hair containing 90% white hair and to the same hair which was permanent waved twice, then a jet of water vapour at 90° C. was applied for 15 to 20 seconds. The hair was then washed with a standard shampoo and then dried.

The hair was dyed chestnut and the difference in colour (selectivity) between the two types of hair was small.

EXAMPLE 6 (Invention)

A dye composition similar to that of Example 5 was used, except that the amounts of aqueous ammonia (containing 22% of $NH_3$) and of monoethanolamine were modified:

| | |
|---|---|
| Aqueous ammonia (containing 22% of $NH_3$) | 0.56 g |
| Monoethanolamine | 12 g |

This composition was mixed weight for weight with 20 volumes of hydrogen peroxide at the time of use.

The mixture obtained above was applied to naturally grey hair containing 90% white hair and to the same hair which was permanent waved twice, then a jet of water vapour at 90° C. was applied for 30 seconds. The hair was washed with a standard shampoo and then dried.

The hair was dyed chestnut and selectivity between the two types of hair was low.

EXAMPLE 7 (Invention)

The following dye composition was prepared at the time of use:

| | |
|---|---|
| Para-phenylenediamine | 1.75 g |
| Para-aminophenol | 0.023 g |
| 1,3-Dihydroxybenzene | 0.417 g |
| Meta-aminophenol | 0.013 g |
| Cetyl/stearyl alcohol (50/50 by weight) | 18 g |
| 2-Octyldodecanol | 3 g |
| oxyethylenated cetyl/stearyl alcohol containing 15 mol of ethylene oxide | 3 g |
| Ammonium lauryl sulphate (30% AM in aqueous solution) | 12 g |
| Monoethanolamime | 12 g |
| 20 volume hydrogen peroxide | 40 g |
| Citric acid qs | pH 6 |
| Demineralized water qs | 100 g |

This composition was applied to naturally grey hair containing 90% white hair and to the same hair which was permanent waved twice, then a jet of water vapour at 90° C. was applied for 3 seconds and the hair was allowed to cool for 10 seconds. The hair was washed with a standard shampoo and then dried.

The hair was dyed dark chestnut and the selectivity between the two types of hair was low.

What is claimed is:

1. A process for the oxidation dyeing of keratinous fibres comprising the step of:

contacting said fibres, said fibres having previously been contacted with a composition containing at least one oxidation dye, in the presence of an oxidizing agent, with a gas containing water vapour, the temperature of the gas being at least 85° C. for a contact time between said gas and said fibres of less than or equal to two minutes.

2. A process according to claim 1, wherein the gas has a temperature ranging from 85° C. to 150° C.

3. A process according to claim 1, wherein the gas is contacted with the fibres for a time period ranging from 0.01 second to less than 2 minutes.

4. A process according to claim 3, wherein the gas is contacted with the fibres for a time period ranging from 0.01 second to 50 seconds.

5. A process according to claim 4, wherein the gas is contacted with the fibres for a time period ranging from 1 second to 10 seconds.

6. A process according to claim 1, wherein the contacting of the fibres with the gas is repeated several times on the fibres.

7. A process according to claim 1, wherein the gas exclusively contains water vapour.

8. A process according to claim 1, wherein the gas contains water vapour and at least one other compound in gas or vapour form.

9. A process according to claim 8, wherein the gas contains water vapour and air.

10. A process according to claim 1, wherein said at least one oxidation dye is an oxidation base or a mixture of at least one oxidation base and at least one coupler.

11. A process according to claim 1, wherein said oxidizing agent is hydrogen peroxide, urea peroxide, an alkali metal bromate or a persalt.

12. A process according to claim 1, wherein said keratinous fibres are human keratinous fibres.

13. A process according to claim 1, wherein the temperature of the gas ranges from 85° C. to less than 100° C.

14. A process according to claim 1, wherein the temperature of the gas ranges from 90° C. to less than 100° C.

* * * * *